United States Patent
Mah et al.

[19]

[11] Patent Number: 6,109,270
[45] Date of Patent: Aug. 29, 2000

[54] MULTIMODALITY INSTRUMENT FOR TISSUE CHARACTERIZATION

[75] Inventors: Robert W. Mah, Cupertino, Calif.; Russell J. Andrews, Manilus, N.Y.

[73] Assignee: The United States of America as represented by the Administrator of the National Aeronautics and Space Administration, Washington, D.C.

[21] Appl. No.: 09/017,519

[22] Filed: Feb. 2, 1998

Related U.S. Application Data

[63] Continuation-in-part of application No. 08/795,272, Feb. 4, 1997.

[51] Int. Cl.$^7$ .................................................. A61B 10/00
[52] U.S. Cl. ........................ 128/920; 128/924; 606/130; 600/562
[58] Field of Search ..................... 600/562, 564, 600/566, 567, 568; 606/1, 130; 128/920, 923, 924, 925

[56] References Cited

U.S. PATENT DOCUMENTS

| | | |
|---|---|---|
| 4,691,715 | 9/1987 | Tanne . |
| 5,226,092 | 7/1993 | Chen ......................................... 382/14 |
| 5,357,955 | 10/1994 | Wolf et al. . |

(List continued on next page.)

FOREIGN PATENT DOCUMENTS

| | | |
|---|---|---|
| 94305152 | 1/1995 | European Pat. Off. . |
| PCT/EP89/ 01362 | 5/1990 | WIPO . |
| PCT/ S96/ 19257 | 6/1997 | WIPO . |

OTHER PUBLICATIONS

C.W. Burckhardt, P. Flury, and D. Glauser, *I.E.E.E. Engineering in Medecine & Biology* (May/Jun. 1995), "Sterotactic Brain Surgery."

Viewgraphs and a set of pictures used in two presentations by Dr. Russell Andrews: (1) at the 1st Asian Congress of Sterotactic, Functional & Computer–Assisted Neurosurgery, in Singapore, on Dec. 11, 1994; and (2) at the International Symposium On Prospective Neurosurgery in the 21st Century, in Japan, on Sep. 22, 1995.

(List continued on next page.)

*Primary Examiner*—Michael Peffley
*Assistant Examiner*—R Kearney
*Attorney, Agent, or Firm*—Robertt M. Padilla; Gary G. Borda; John G. Mannix

[57] ABSTRACT

A system with multimodality instrument for tissue identification includes a computer-controlled motor driven heuristic probe with a multisensory tip. For neurosurgical applications, the instrument is mounted on a stereotactic frame for the probe to penetrate the brain in a precisely controlled fashion. The resistance of the brain tissue being penetrated is continually monitored by a miniaturized strain gauge attached to the probe tip. Other modality sensors may be mounted near the probe tip to provide real-time tissue characterizations and the ability to detect the proximity of blood vessels, thus eliminating errors normally associated with registration of pre-operative scans, tissue swelling, elastic tissue deformation, human judgement, etc., and rendering surgical procedures safer, more accurate, and efficient. A neural network program adaptively learns the information on resistance and other characteristic features of normal brain tissue during the surgery and provides near real-time modeling. A fuzzy logic interface to the neural network program incorporates expert medical knowledge in the learning process. Identification of abnormal brain tissue is determined by the detection of change and comparison with previously learned models of abnormal brain tissues. The operation of the instrument is controlled through a user friendly graphical interface. Patient data is presented in a 3D stereographics display. Acoustic feedback of selected information may optionally be provided. Upon detection of the close proximity to blood vessels or abnormal brain tissue, the computer-controlled motor immediately stops probe penetration.

21 Claims, 7 Drawing Sheets

U.S. PATENT DOCUMENTS

| | | |
|---|---|---|
| 5,415,169 | 5/1995 | Siczek et al. . |
| 5,463,548 | 10/1995 | Asada et al. ........................ 364/413.02 |
| 5,526,822 | 6/1996 | Burbank et al. . |

OTHER PUBLICATIONS

Abstract of the presentation at the 1st Asian Congress of Sterotactic, Functional & Computer–Assisted Neurosurgery, on Dec. 11, 1994.

Abstract of the presentation at the International Symposium On Prospective Neurosurgery in the 21st Century, on Sep. 22, 1995.

"Neural Network Design", Hagan, M.T., Demuth, H.B., Beale, Mark, Neural Network Design, PWS Publishing Company, 1996, chapter 12, pp. 12–1 to 12–49, "Variations on Backpropagation"; chapter 14, pp. 14–12 to 14–38, "Feature Maps"; and chapter 19, pp. 19–1 to 19–12, "Epilog".

"Signal and Image Processing Using Neural Networks—A C++ Sourcebook," Masters, T., chapter 1, pp. 1 to 10, Wiley, 1994.

"Advanced Algorithms for Neural Networks—A C++ Sourcebook," chapter 3, pp. 135 to 156, Masters, T., Wiley, 1995.

"Neural Networks for Control", Miller, T.W., Sutton, R.S., and Werbos, P.J., Chapter 5 by Narendra, K.S., pp. 115 to 142, MIT Press, 1995.

MULTIMODALITY INSTRUMENT FOR TISSUE CHARACTERIZATION

This application is a CIP of 08/795,272 filed on Feb. 4, 1997.

ORIGIN OF THE INVENTION

The invention described herein was made by employees of the United States Government and may be manufactured and used by or for the Government for governmental purposes without payment of any royalties thereon or therefor.

BACKGROUND OF THE INVENTION

1. Technical Field of the Invention

The present invention relates in general to the field of sensors and instruments, and it particularly relates to medical diagnostic, prognostic, treatment and surgical instruments. This invention further relates to a system which heuristically provides tissue identification in neuroendoscopy and minimally invasive brain surgery.

2. Description of the Prior Art

Existing medical instruments provide general diagnoses for the detection of tissue interface such as normal tissue, cancer tumor, etc. However, such detection has been limited clinically to tactile feedback, temperature monitoring, and the use of a miniature ultrasound probe for tissue differentiation during surgical operations. Stereotactic computed tomography (CT) scanners, magnetic resonance imaging (MRI) devices, and similar other instruments provide guided brain biopsy and preoperative scans for use in neurosurgical surgeries. These scans allow samples of brain tissue to be obtained with some degree of accuracy.

However, existing devices provide diagnostic data of limited use, particularly in neurosurgery, where the needle used in the standard stereotactic CT or MRI guided brain biopsy provides no information about the tissue being sampled. The tissue sampled depends entirely upon the accuracy with which the localization provided by the pre-operative CT or MRI scan is translated to the intracranial biopsy site. Any movement of the brain or the localization device (e.g., either a frame placed on the patient's head, or fiducials/anatomical landmarks which are in turn related to the preoperative scan) results in an error in biopsy localization. Also, no information about the tissue being traversed by the needle (e.g., a blood vessel) is provided. Hemorrhage due to the biopsy needle severing a blood vessel within the brain is the most devastating complication of stereotactic CT or MRI guided brain biopsy.

Several other drawbacks are associated with existing devices in stereotactic CT or MRI guided brain biopsy. For instance, this procedure is labor intensive and requires the transfer of localization coordinates from the preoperative scan to the localization device. The depth to which the needle is passed within the brain is also subject to human error. No real-time information is gained about either the tissue being biopsied or the tissue being traversed en route to the biopsy site. The biopsy information is not provided on a real-time basis, and may take a day or more for various staining procedures to be performed by the neuropathologist on the sampled tissue. The non-simultaneity of the sampling, analysis and use precludes existing stereotactic CT and MRI guided brain biopsy from being performed remotely, such as in space missions, long term space exploration travels, or hospitals that are not staffed with a neurosurgeon.

CT and MRI scans allow neurosurgeons to identify anatomical regions of the brain with an accuracy on the order of one or two millimeters. As presented later, these scans are not adequate for the precise localization needed by neurosurgeons to perform optimally safe surgery.

CT and MRI scans are obtained pre-operatively. In a conventional stereotactic CT or MRI guided brain biopsy, a frame is applied to the patient's head and the scan obtained. The coordinates of the desired targets on the scan are then translated to corresponding coordinates of the frame. The patient then undergoes the biopsy through a small hole drilled in the skull (three or four millimeters in diameter) using a plastic or metal biopsy "needle" that most commonly aspirates a very small core of tissue (on the order of one or two millimeters in diameter by three or four millimeters in length). Any movement of the brain, such as can be due to changing the position of the patient from the position in which the scan was obtained, can introduce error into the biopsy coordinates.

A much greater practical problem arises when the pre-operative scan is used to guide the removal of a tumor deep within the brain. As the tumor is removed, or the brain retracted to permit access to the tumor, the coordinates from the pre-operative scans become somewhat invalid. This error is especially troublesome with recently developed systems that use an optically-encoded "arm" in an electro-optical camera system for localization during neurosurgical operations.

Another significant problem with using CT and MRI scans for localization is that they do not provide functional localization. As neurosurgical procedures become more precise, the need increases for knowledge of the functional organization of the brain. The localization necessary to perform pallidotomy procedures for Parkinson's disease is one example where anatomical localization based on CT or MRI scanning is inadequate for optimal treatment, since electrophysiological mapping intraoperatively is important to maximize the benefit of the operation for a given patient.

There have been a few recent advances in pre-operative scanning that provide some information about the functional organization of the brain. Functional MRI and PET (Positron Emission Tomography) are two examples of such recent scanning techniques. However, these scanning techniques are hampered either by their limited range of functions which can be utilized (e.g., functional MRI) or their relatively poor resolution, for example on the order of one half to one centimeter (e.g., PET).

SUMMARY OF THE INVENTION

It is an object of the present invention to enable the placement of multiple neurosurgical sensors and/or effectors (or tools), such as a biopsy probe in any desired region of the brain with extreme accuracy.

Another object of the present invention is to enable the localization of the neurosurgical sensors and/or effectors based on the characteristics of the local brain environment, taking into consideration the anatomical and functional variability among human (and non-human) brains.

Still another object of the present invention is to perform minimally invasive surgery, for example the localized placement of the effector and treatment with minimal disruption of normal brain functions. An important method for minimizing invasiveness is miniaturization.

Yet another object of the present invention is the automation of part of surgical procedures. This objective is realized by incorporating two disciplines. The first discipline is robotics and remote control, and the second discipline is neural net (or artificial intelligence) learning. Remote control has been used by NASA scientists in missions either too dangerous or impossible for human performance, such as sending an unmanned submarine beneath the Antarctic ice cap and a robotic rover into an Alaskan volcano crater. Neural net learning allows a computer to gather information from repeated exposures to normal and abnormal brain tissue which can then be applied to a novel situation, in order to decide the type of tissue being encountered.

A further object of the present invention is to provide a heuristic robotic system with a multimodality instrument for tissue identification. This instrument will replace "dumb" metal needles used to perform exploratory surgeries such as biopsies. It will also help avoid certain complications associated with the translation of the lesion (e.g., tumor) coordinates from MRI/CT scans to the actual lesion using the inventive multimodality instrument. These complications include the inability to obtain tissue which will allow the neuropathologist to make a diagnosis, and the risk of severing a blood vessel which may result in a hemorrhage causing significant neurological injury or possibly death.

Briefly, the foregoing and other features and advantages of the present invention are realized by a robotics system with a multimodality heuristic instrument for tissue identification. The instrument includes a computer-controlled motor driven probe with a multisensory tip, e.g., a group of sensors may be selectively incorporated into the probe tip, or near the probe tip or as part of the probe.

In a preferred embodiment, the probe is driven by a computer-controlled actuator mechanism to the appropriate depth within the brain for obtaining a continuous and real time output of resistance or density of the tissue being penetrated. This output is received into a neural net learning program which is constantly learning not only the differences between normal brain tissue and abnormal brain tissue, such as tumors, but also the differences between various regions of the brain (e.g., gray matter versus white matter).

In another embodiment where robotic insertion is not advantageous, the probe can be a hand-held device and/or manually driven instead of motor driven.

The instrument further includes a micro laser-Doppler blood flow probe having a diameter of less than approximately 1 mm. This probe detects blood vessels before it can disrupt them, and it can further catalog the blood flow differences between either normal brain tissue, abnormal brain tissue, or various regions of the brain such as gray matter and white matter (which are known to have a roughly fivefold difference in blood flow). A micro ultrasound probe, also less than approximately 1 mm in diameter, can aid in blood vessel detection and tissue identification. A $pO_2$ (partial pressure of oxygen) microprobe, less than 1 mm in diameter can aid in the detection of hypoxia which is an indication of turner malignancy.

Ion-selective micro electrodes can also be used to monitor such important parameters as pH, calcium, sodium, potassium, and magnesium. Additionally, optical fluorescence and/or optical absorbance probes with a diameter of less than approximately 1 mm can also be used to monitor oxygen and carbon dioxide levels and other parameters of the signal. The combination of optical reflectance sensors and neural net learning to characterize the tissue being penetrated by the probe yields a characteristic optical reflectance signature which is very valuable in distinguishing and identifying different tissues, such as blood vessels, tumors, grey matter and white matter.

The present multimodality instrument offers several advantages and can be used in various commercial applications. For example, the present instrument improves the diagnostic accuracy and precision of general surgery, with near term emphasis on stereotactic brain biopsy. It automates tissue identification with emphasis on stereotactic brain biopsy to permit remote control of the procedure. It also reduces morbidity of stereotactic brain biopsy. The present instrument may also be used in conjunction with various surgical tools to increase the safety, accuracy and efficiency of surgical procedures. For example, the use of the multimodality instrument for monitoring patients with severe head injuries would greatly enhance the surgeon's capabilities in neurosurgery.

The present instrument may also be used in conjunction with endoscopes for tissue identification in various types of surgery, and can be adapted to a hand held device and/or manually driven instead of motor driven for procedures where the automated robotic aspect is not advantageous.

The present instrument may be used in a variety of applications including but not limited to tumor ablation in neurosurgery, general exploratory surgery, prostate cancer surgery, breast cancer surgery, spinal surgery automated tissue identification for general surgery use (e.g., detecting the interface between normal tissue, cancer, tumor, or other lesion), automated stereotactic biopsy for neurosurgery, continuous monitoring for patients at risk for cerebral ischemia and/or increased intracranial pressure (e.g., many patients with cerebrovascular disease, tumors, or severe head injury), and other surgical procedures that could be performed in an automated/robotic fashion for minimizing trauma to the patient because of decreased exposure time in comparison with procedures performed manually and/or more invasively.

BRIEF DESCRIPTION OF THE DRAWINGS

The above and other features of the present invention and the manner of attaining them will become apparent, and the invention itself will be best understood, by reference to the following description and the accompanying drawings, wherein.

Similar numerals refer to similar elements in the drawing. It should be understood that the sizes of the different components in the drawings are not in exact proportion, and are shown for visual clarity and for the purpose of explanation.

DETAILED DESCRIPTION OF THE PREFERRED EMBODIMENTS

Figure 1:
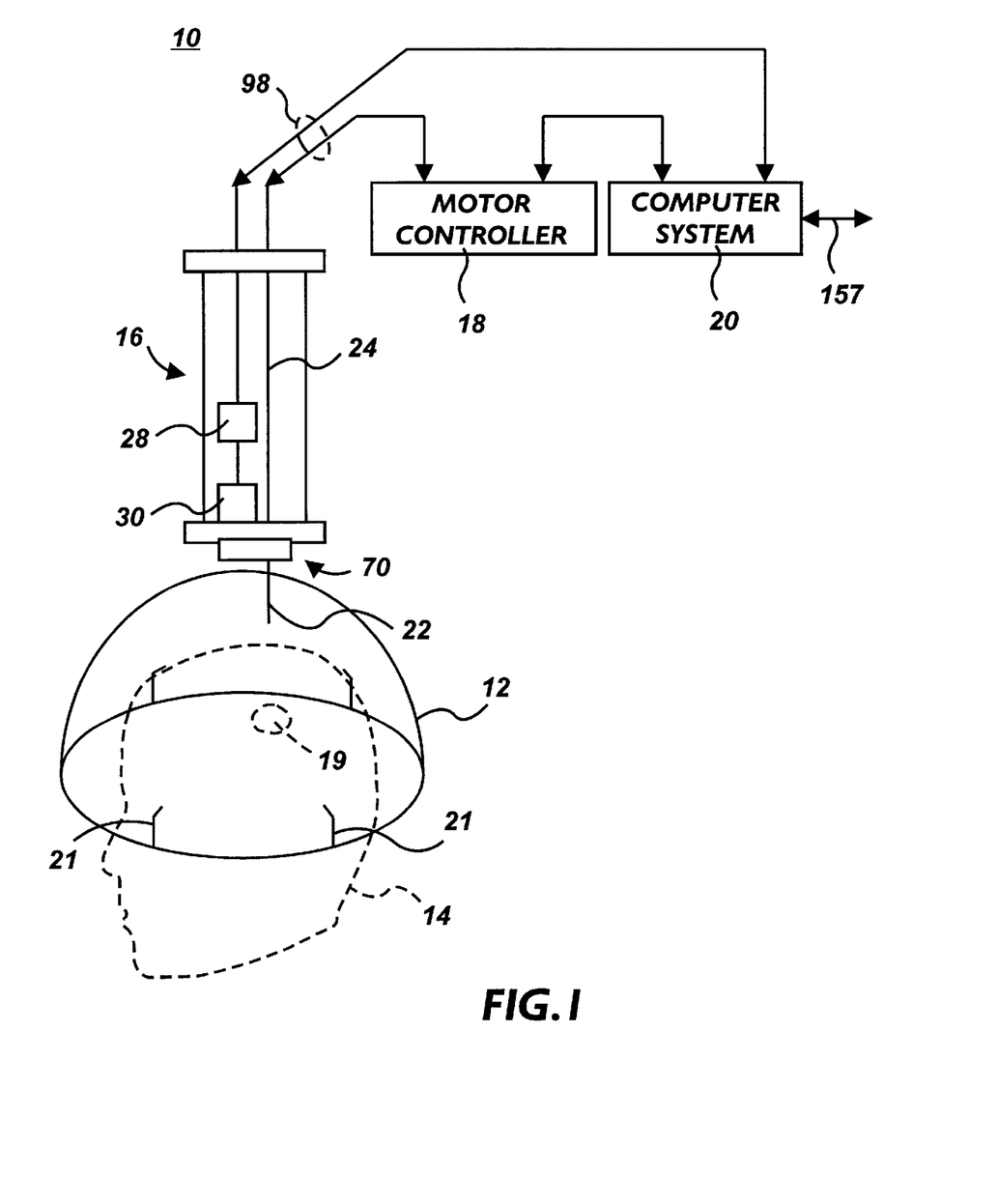
FIG. 1 is a perspective schematic view of a robotic system configuration incorporating a multimodality instrument (shown schematically) according to the present invention.

FIG. 1 illustrates a robotics heuristic system 10 configured pursuant to the present invention. The system 10 generally includes a stereotactic device 12 mounted on a subject's head 14; a robotics instrument 16; motor controller 18; and a computer system 20. While the system 10 will be described in connection with a neurosurgical application, it should be clear that the system 10 may be adapted for use in various other medical and non medical applications.

The stereotactic device 12 is mounted on the subject's head 14 and is affixed to the skull by means of retaining screws or pins 21. The stereotactic device 12 further assists in locating a target site, for example a brain tumor 19, by providing a fixed reference or fiducial coordinate system. The stereotactic device 12 is well known in the field and is commercially available from Radionics, under the trade name BRW/CRW stereotactic systems. In other applications the stereotactic device 12 may be replaced with another suitable fixation device, such as a "helmet" which conforms precisely to the subject's head 14, and/or a device, such as an optical system that can be referenced to the preoperative CT or MRI scan.

The robotic instrument 16 is mounted on the stereotactic device 12, and enables one or more sensors and/or one or more tools to be handled in a precisely controlled fashion. In the present illustration for instance, a cannula 22 (within which a probe 24 is lodged) is designed to automatically penetrate the subject's brain with an extremely high degree of precision. In another embodiment, the probe-cannula assembly 27 also shown in FIG. 3 and formed of the cannula 22 and the probe 24 can be replaced with a probe-tool assembly wherein the tool is capable of performing various mechanical functions and medical treatment.

The robotic instrument 16 includes an actuator mechanism 26 capable of driving the sensors and/or tools with minimal damage to the brain tissue. In the present illustration the actuator mechanism 26 includes two stepper motors 28, 30 that automatically drive the probe 24 inside the cannula 22, and that further drive the probe-cannula assembly 27 into the brain tissue.

The actuator mechanism 26 is controlled by the motor controller 18 and the computer system 20. The computer system 20 further includes a neural network program (comprised of a combination of neural networks) used to adaptively learn the information derived by the instrument 16, for instance resistance and image features of normal brain tissue during the surgery. Fast learning neural networks are used to provide near real-time modeling, and a fuzzy logic interface to the neural network program is used to incorporate expert medical knowledge in the learning process. Identification of abnormal brain tissue is determined by the detection of change and comparison with previously learned models of abnormal brain tissues. Where the automated robotic aspect is not advantageous the drive mechanism may be replaced with a manually-driven mechanism or inserted directly by hand.

Figure 2:
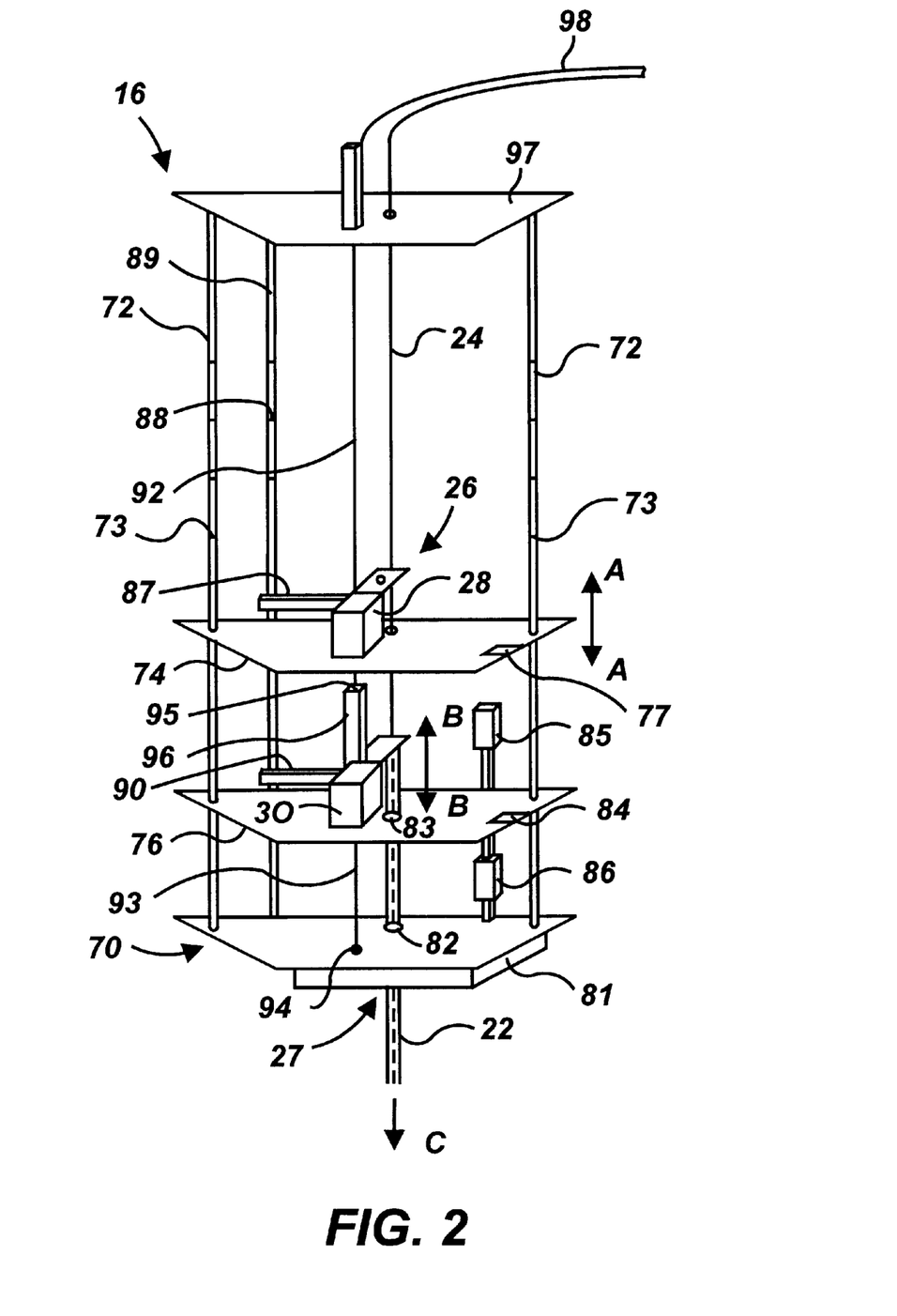
FIG. 2 is an enlarged view of the instrument shown in FIG. 1.

The components of the robotics heuristic system 10 will now be described in greater detail in connection with FIGS. 2, 3 and 4. Starting with the instrument 16, it is comprised of a mounting structure 70; two guide rails 72; a probe mounting plate 74; a cannula mounting plate 76; the actuator mechanism 26; the cannula 22; and the probe 24.

The mounting structure 70 generally includes a base 81 that removably and adjustably mates with the stereotactic device 12 and provides a mounting interface for the actuator mechanism 26. The base 81 may be made of any suitable light weight material, such as aluminum, and may assume various shapes that best suit the application for which it is used. The base 81 includes an opening 82 that serves as a guide for the cannula 22.

The two guide rails 72 serve as a guide mechanism, and extend from the base 81 and serve as guides for the probe mounting plate 74, for it to translate slidably along a desired direction with minimal or no pitch or roll deviation. The rails 72 may include markings 73 for providing a visual indication as to the position of the probe 24 relative to the base 81. It is conceivable to replace the two rails 72 with an appropriate guide mechanism for the actuator mechanism 26. In another embodiment the guide mechanism allows the actuator mechanism 26 to rotate around one rail 72 and to further translate linearly in one or more predetermined direction.

The probe mounting plate 74 provides a means for securely holding the motor 28 and the probe 24. The probe mounting plate 74 includes two adjacent openings through which the probe mounting plate 74 is allowed to journey slidably along the rails 72 for translation along the direction of the arrow A—A. In one exemplary illustration the direction of the arrow A—A coincides substantially with the vertical direction. One or more strain gauges 77 may be secured to the upper surface and/or lower surface of the probe mounting plate 74 to measure pressure or another parameter acting on the cannula 22 or the probe 24.

As a safety feature, an adjustable mechanical stop 85 is mounted on the base 81 to limit the amount of travel of the probe 24 in and through the cannula 22. For example, it is possible to initially limit the probe insertion into the cannula 22 up but not exceeding the tip of the cannula 22. Subsequently, the mechanical stop 85 can be adjusted to allow the probe to extend beyond the cannula tip to another limit for the purpose of deploying a probe effector.

The cannula mounting plate 76 provides a means for securely holding the cannula 22. The cannula mounting plate 76 includes an opening 83 through which the cannula 22 is inserted for translation in the direction of the arrow B—B. In this exemplary illustration the direction of the arrow B—B coincides with that of the arrow A—A, though it is conceivable to design the system 10 such that the probe 24 and the cannula 22 translate along two different directions, at least before they mate.

The cannula mounting plate 76 serves as a retention guide to the cannula 22 and is adjustably moveable relative to the base 81 along the direction of the arrow B—B. One or more strain gauges 84 may be secured to the upper surface and/or lower surface of the cannula mounting plate 76 to measure pressure or another parameter.

The cannula mounting plate 76 also serves as a safety mechanism for limiting the travel of the probe-cannula assembly 27 beyond a predetermined level inside the brain. To this end, as the cannula mounting plate 76 reaches the base 81, or a predetermined distance above the base 81, it stops the advancement of the cannula 22 inside the brain tissue. The distance between the cannula mounting plate 76 and the base 81 may be adjusted even when the cannula mounting plate 76 has reached a predetermined position, by means of an adjustable mechanical stop 86 provided for limiting the travel of the cannula mounting plate 76.

A position encoder 87 may be mounted on the probe mounting plate 74 to provide information on the position of the probe 24 relative to a reference mark on the base 81, or relative to markings 88 on a graded ruler 89. Similarly, a position encoder 90 may be mounted on the cannula mounting plate 76 to provide information on the position of the cannula 22 relative to the reference mark on the base 81, or relative to markings 88 on the ruler 89.

The actuator mechanism 26 includes the two motors 28, 30 and their corresponding lead screws 92 and 93, respectively. The motor 30 is a stepper motor as is generally known in the field. In this particular illustration the motor 30 is available from Air Pax Corporation, in California, as model number L 9 2211-P2. The motor 28 is generally similar to the motor 30. It should however be clear that another suitable drive mechanism may alternatively be used to drive the cannula 22 by itself or in combination with the probe 24.

The motor 30 is fixedly secured to the cannula mounting plate 76 via the motor housing, and is further secured to the base 81 by means of the lead screw 93. To this effect, one end 94 of the lead screw 93 is affixed to the base 81, and the opposite end of the lead screw 93 is free. The housing of the motor 30 traverses the lead screw 93. As the motor 30 runs, it causes its housing to translate linearly in the direction of the arrow B—B, thus driving the cannula mounting plate 76 and the cannula attached thereto.

The lead screw 92 extends through the housing of the motor 28 and the probe mounting plate 74, and operates similarly to the lead screw 93. One end 95 of the lead screw 92 is affixed to the cannula mounting plate 76, the housing of the motor 30, or to a guide 96 extending from, and secured to the probe mounting plate 74. The opposite end of the lead screw 92 is affixed to a top base plate 97. As the motor 28 runs, the housing of motor 28 traverses the lead screw 92 to move linearly in the direction of the arrow A—A, thus driving the probe mounting plate 74 and the probe 24 attached thereto toward the cannula 22.

The cannula 22 is a hollow tubular member that is known in the field. The cannula 22 and the probe 4 are available from Chorus, located in Minnesota, as models 2120 and Archo PEN. The cannula 22 may include markings that provide the surgeon with a visual indication as to the insertion progress of the probe-cannula assembly 27 within the brain tissue. In another embodiment the cannula 22 may be replaced with a suitable guide mechanism or eliminated all together.

The probe 24 is a multimodality probe and is tightly secured to the probe mounting plate 74. The probe 24 is connected to a power, signal and data cabling 98 that electrically and/or optically connects the instrument 16 to the motor controller 18 and the computer system 20. The cabling 98 is supported mechanically by any suitable support means (not shown) to prevent the cabling 98 from excessive bending.

Figure 3:
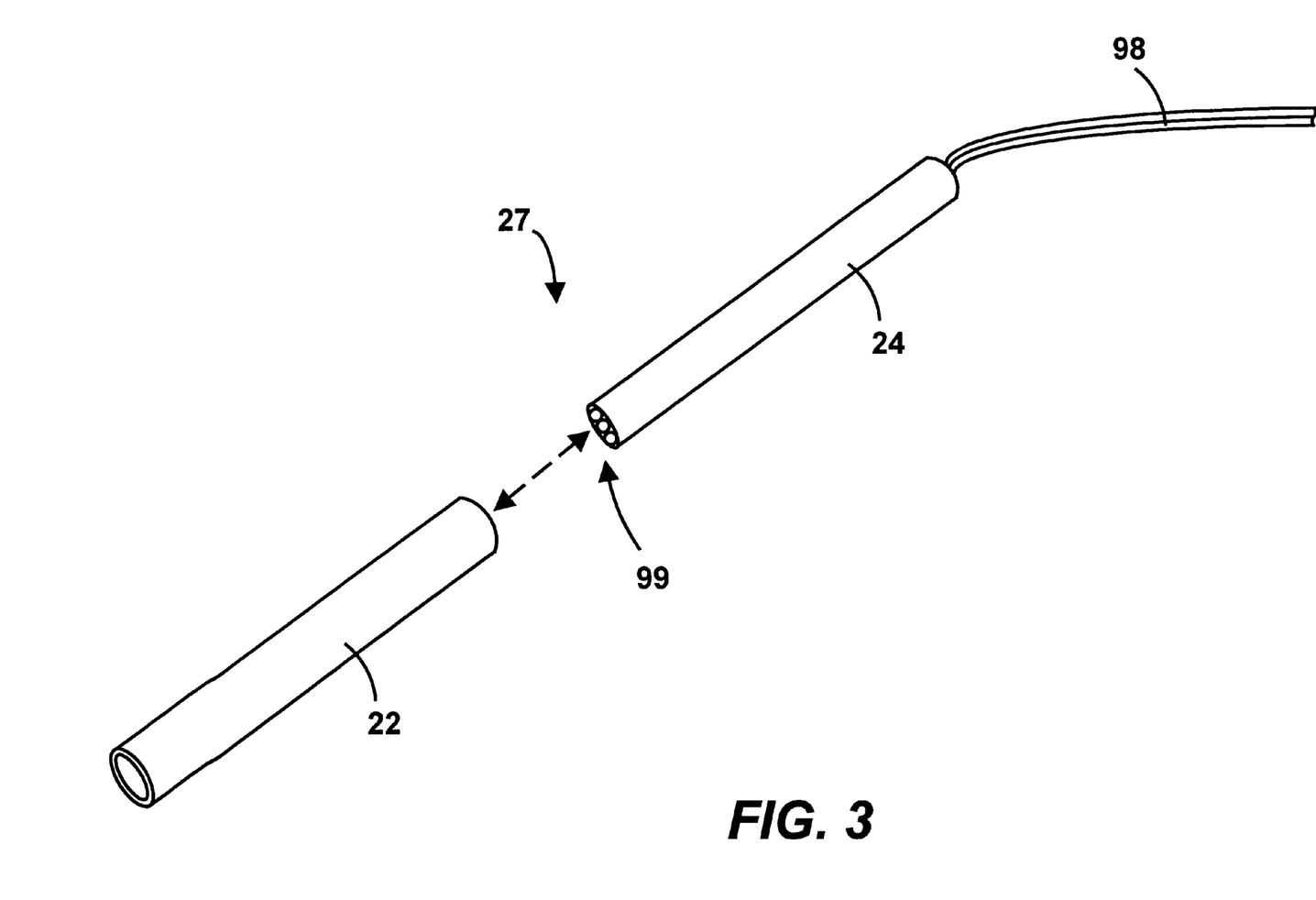
FIG. 3 is a greatly enlarged view of a probe-cannula assembly comprised of a multimodality probe and a cannula for use in the instrument of FIGS. 1 and 2.

As illustrated in FIG. 3, the probe 24 may include one or more of the following sensors and/effectors (or tools) 99, although the following or other types of sensors and/or tools may alternatively be used depending on the application for which they are used:

Strain gauge for measuring the penetration resistance. For example, the strain gauge is available from Entran Devices Corporation, located in New Jersey, as model number EPIH-111-100P/RTV.

Wick in needle microprobe for measuring interstitial pressure.

Laser Doppler blood flow sensor for measuring the proximity of the blood vessels to the cannula tip as well as the rate of blood flow. For example, the laser Doppler blood flow sensor is available from VASAMEDICS, located in Minnesota, as model number $BPM^2$.

Ultrasound probe for tissue identification.

Endoscope for providing image data. For example, the endoscope is available from Johnson & Johnson Professional, Inc., as model number 83-1337.

$pO_2$ (partial pressure of oxygen) microprobe for measuring hypoxia.

Laser and/or other optical sensors for measuring the reflectance properties of tissues.

Temperature sensor to measure tissue temperature.

Ion specific sensors to measure the concentration of specific ions.

Microelectrode to measure brain electrical activity.

Tissue ablation laser.

Effectors such as: biopsy forceps, malleable biopsy forceps, grasping forceps, micro-scissors, coagulator, irrigator.

Figure 5A:
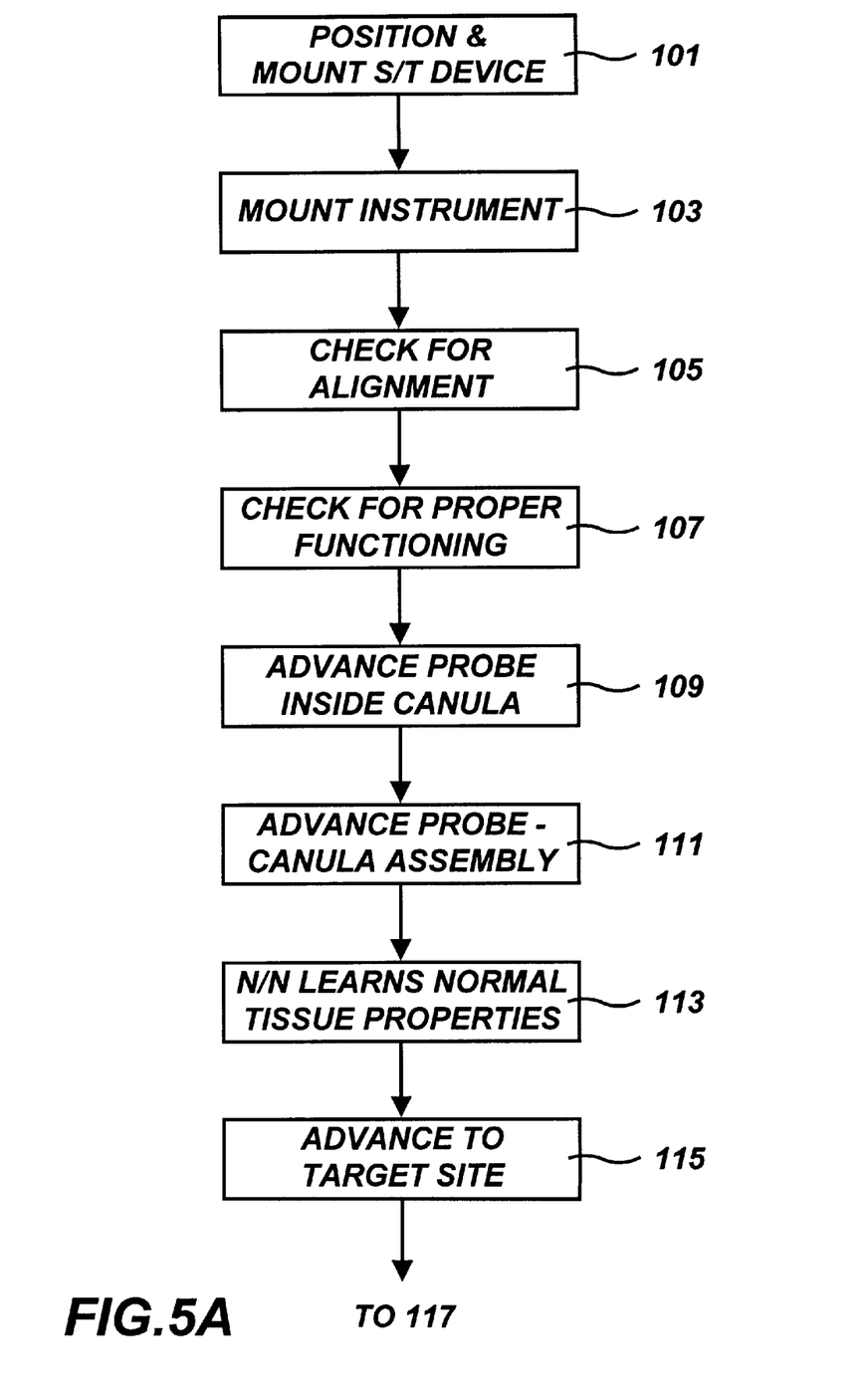
FIGS. 5A and 5B represent a flow chart illustrating the general use of the robotic system of FIG. 1.
Figure 5B:
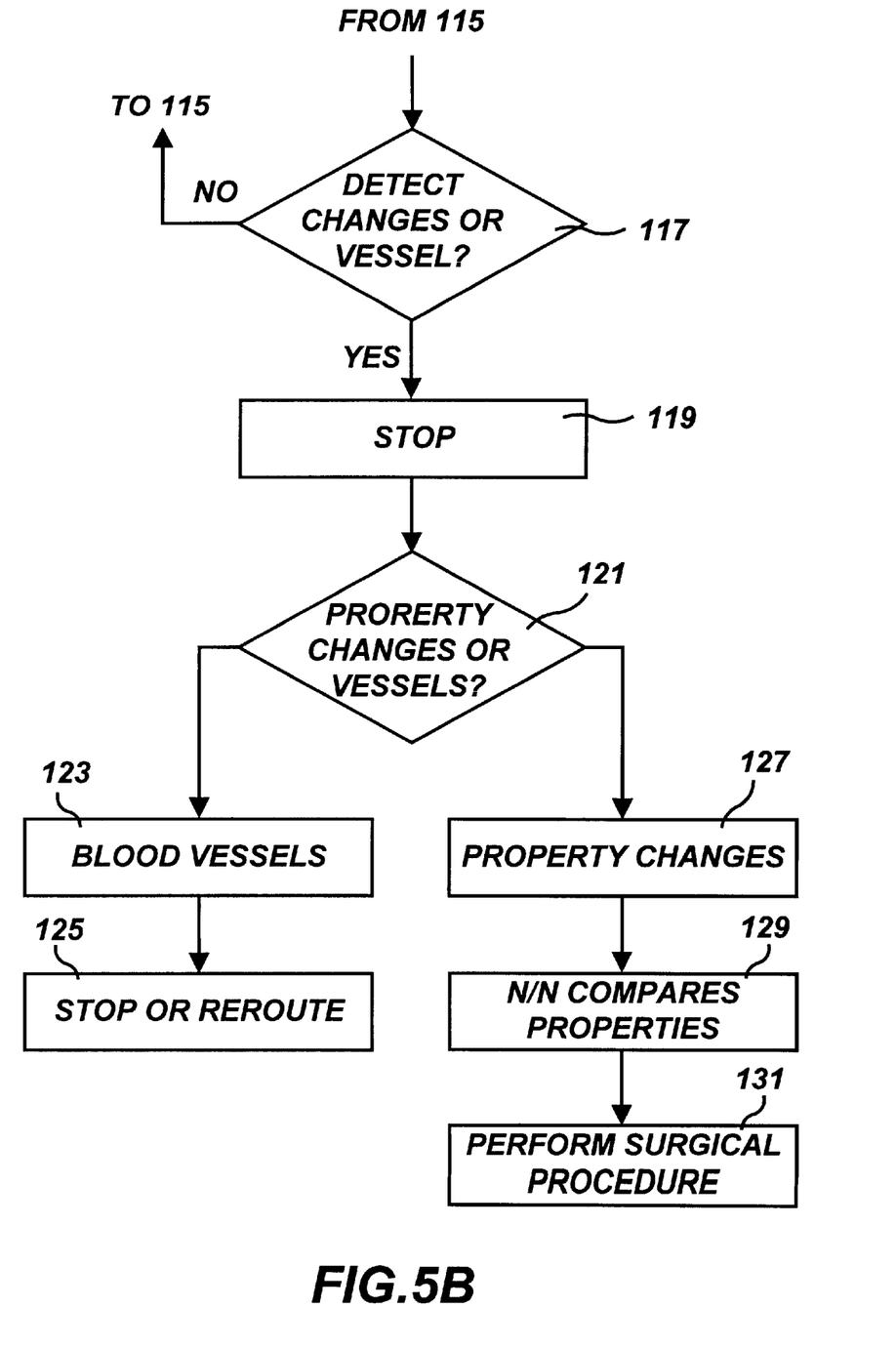

The general use and operation of the system 10 will now be described in connection with FIGS. 5A and 5B. The surgeon starts by positioning the stereotactatic device 12 on the subject's head 14. The stereotactic device 12 which is then mounted and tightly secured in place (block 101). A CT or MRI scan can be obtained with the stereotactic device 12 in place is used to relate the procedure to a prior CT or MRI scan. A hole may be drilled in the subject's skull at a predetermined site, either manually or robotically using the system 10.

Having selected the proper sensors and/or tools forming part of the probe 24, the surgeon mounts the instrument 16 on the stereotactic device 12 (block 103) and calibrates the instrument 16, by checking the alignment of the probe 24 relative to the cannula 22 (block 105) and then checking the proper functioning of the instrument 16, the motor controller 18 and the computer system 20 (block 107).

With the motor 30 in a non-operative mode and the cannula mounting plate 76 stationed at a predetermined marking 88, the surgeon advances the probe 24 toward the cannula 22 (block 109) by means of the motor 28, until the probe 24 is housed in its proper position within the cannula 22. At which time the motor 28 is locked in position. In some embodiments of the system 10 it is desirable to have the tips of the probe 24 and the cannula 22 flush with each other, while in other embodiments, such as when tools are used, the tips of the probe 24 and the cannula 22 are not flush. As an example, the tip of the probe 24 may extend beyond the tip of the cannula 22.

Once the calibration stage is completed the surgeon starts the surgical stage by instructing the computer system 20 to advance the probe-cannula assembly 27 into the brain normal tissue (block 111) at a predetermined controlled speed. The advancement of the probe-cannula assembly 27 is performed by operating the motor 30, which causes the probe mounting plate 74, the motor 28, the cannula mounting plate 76, and the probe-cannula assembly 27 to be driven simultaneously forward in the direction of the arrow C.

As the probe-cannula assembly 27 is advancing into normal tissue the neural network program within the computer system 20 learns the properties of the normal tissue (block 113) for further processing, as will be described later. In certain applications it might be desirable to stop the advancement of the probe-cannula assembly temporarily until sufficient data is collected or to provide the neural networks of the computer system 20 sufficient time to learn.

When either the surgeon or the computer system 20 determines that sufficient data have been collected, the actuator mechanism 26 is instructed to advance the probe-cannula assembly to a predetermined target site (115), for example tumor 19. The computer system 20 continually checks to determine whether changes in the tissue properties or blood vessels have been detected (block 117). If the computer system 20 does not detect property changes or blood vessels, it instructs the probe-cannula assembly 27 to continue its travel toward the target site (block 115). If on the other hand the computer system 20 detects property changes or blood vessels then it instructs the probe-cannula assembly 27 to stop advancing (block 119).

Based on the detection result (block 117) the computer system 20 notifies the surgeon of the appropriate action to be taken. As an example, the computer system 20 determines whether it has detected tissue property changes or blood vessels (block 121). If the computer system 20 detects the proximity of blood vessels then the surgeon takes the appropriate corrective measures, such as to stop the surgery or to reroute the probe-cannula assembly 27 (block 125). These corrective measures will enable the surgeon to avoid injury to the blood vessels.

If however, the computer system 20 detects tissue property changes (block 127), the neural networks compare the measured tissue properties and/or measured changes in tissue properties to previously learned properties and to reference properties (block 129). At this stage the surgeon will confidently perform the necessary surgical procedure (block 131).

A few exemplary surgical procedures that can be performed using the system 10 are:

Automated tissue identification for general surgery use, for detecting the interface between normal tissue, cancer, or tumor. For example, surgery to remove prostate cancer can be accomplished accurately with minimal damage to normal tissue.

Automated stereotactic biopsy for neurosurgery.

Continuous monitoring for patients at risk for cerebral ischemia and/or increased intracranial pressure.

With the development of multimodality effectors as well as multimodality sensors on the neurosurgical probe, many neurosurgical procedures could be performed in an automated/robotic fashion, thus minimizing trauma to the brain tissue because of the decreased exposure needed in comparison to open procedures performed by a neurosurgeon manually. Examples include the precise placement of (a) electrodes (epilepsy), (b) chemotherapeutic agents or radiation seeds (brain tumors), and (c) transplanted tissue (movement disorders such as Parkinson's disease). Increased precision of intraoperative localization and excision (or ablation with a laser beam) of deep brain lesions would be possible.

In vivo injection of chemicals and tissue.

Scientific and animal research.

In one embodiment of the system 10, once the target site has been detected and reached, the sensing probe 24 is retracted from the cannula 22 by reversing the operation of the motor 28. A substitute probe, for instance a probe 24 containing tools, can then be positioned inside the cannula 22 as described above, for aiding in the surgical procedure.

For neurosurgical biopsy applications, the instrument 16 is mounted on the stereotactic frame 12 in order to have the biopsy probe 24 penetrate the brain in a precisely controlled fashion. The resistance of the brain tissue being penetrated is monitored by a miniature (e.g., 0.050 inch-diameter) circular strain gauge 99 attached to the tip of the biopsy probe 24. Other modality sensors such as a miniature endoscope or laser Doppler blood flow sensor are mounted near the probe tip to provide real-time tissue images and the ability to detect the proximity of blood vessels.

One embodiment of control circuitry is the motor controller 18 which drives, and precisely controls the motors 28, 30. In a preferred embodiment the motor controller 18 includes a circuit board that includes control logic for generating commands. The motor controller 18 is available from Motion Engineering, Inc., located in California, as model number PCX/DSP-800. The motor controller 18 further includes an amplifier that generates the electrical current to drive the motors. The amplifier is available from Haydon Switch & Instrument, Inc., located in Connecticut, as part number 39105. Some or all of the motor controller 18 may be installed internally or externally relative to the computer system 20.

Figure 4:
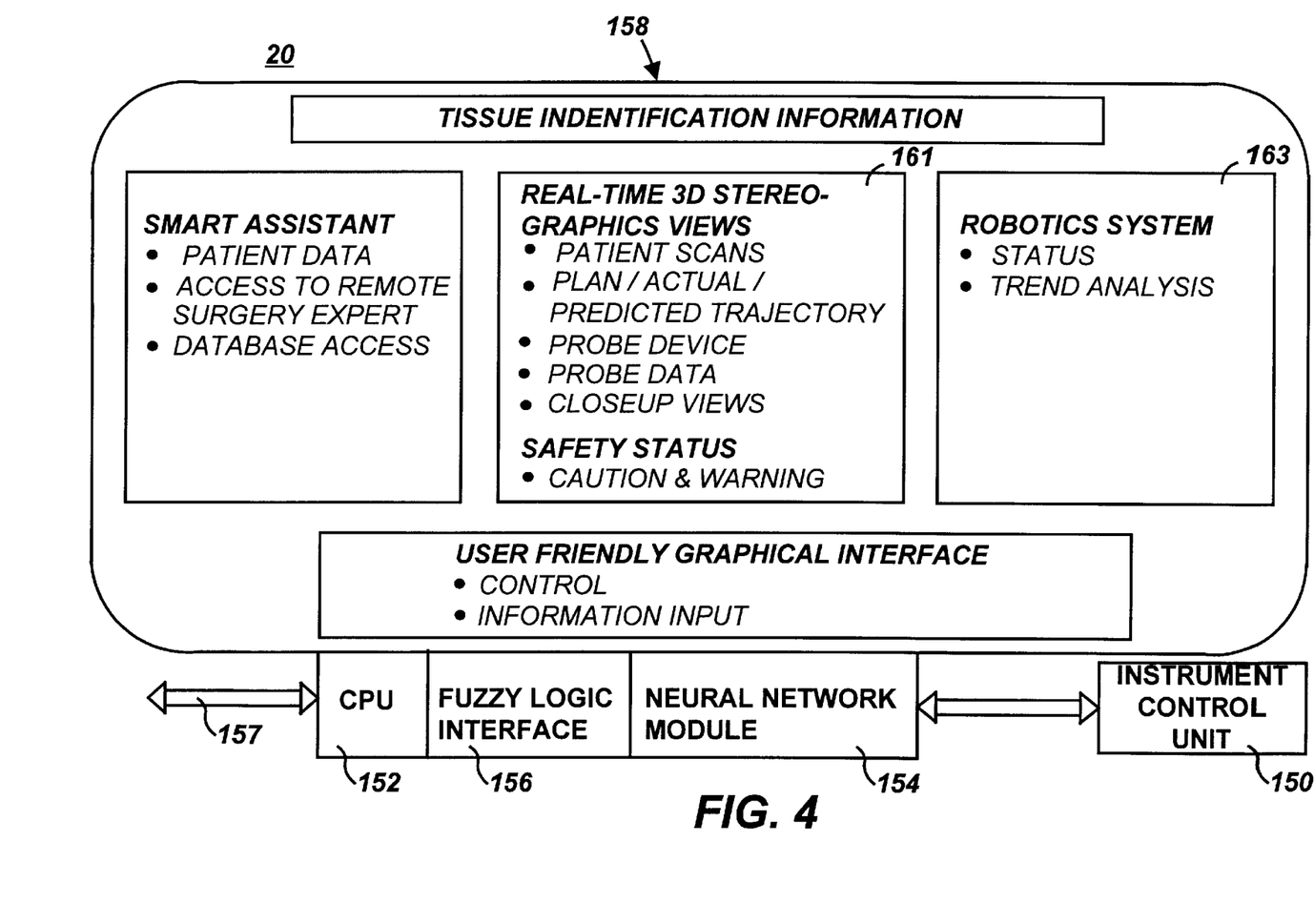
FIG. 4 is a schematic view of a monitor forming part of the robotic system of FIG. 1, illustrating an exemplary user interface graphics display forming part of a computer system.

With reference to FIG. 4, the computer system 20 generally includes an instrument control unit 150, a central processing unit (CPU) 152, a neural network module 154, a fuzzy logic interface 156, and a three-dimensional (3D) graphics interface 158.

The instrument control unit 150 controls the various sensors and tools and performs signal processing for the various sensors and tools of the probe 24. As an example, the instrument control unit 150 can change the brightness and contrast of images generated by an endoscope; change the sensitivity of a laser Doppler; switch laser sources; interpret reflectance signals; turns tools ON and OFF, etc.

The CPU 152 may have any suitable speed, for example 200 MHZ, for acquiring data, signal processing; controlling the graphics display; and providing a user friendly interface. The computer system 20 may be connected via a suitable communication link 157 to remote computers or other systems, which, for example enable the remote operation and control of the system 10.

The neural network module 154 is used to adaptively learn the information provided by the instrument 16. As an example, the neural network module 154 can learn the characteristics of a particular subject's normal brain tissue, such as resistance, color, size, shape, patterns, reflectance and other factors associated with the various types of sensors and tools listed herein, while the surgery is being performed. Fast learning neural networks are used to provide near real-time modeling. The fuzzy logic interface 156 is added to the neural networks to incorporate expert medical knowledge in the learning process.

Neural networks have described in several publications, for instance "How Neural Networks Learn from Experience", by G. H. Hinton, Scientific American, September 1992, pages 145–151. However, the combination of various neural networks and the fuzzy logic interface 156 to automatically conduct important aspects of complicated surgical processes telemetrically, interactively with the surgeon, and with minimal risks to the patients is believed to be new.

Figure 6:
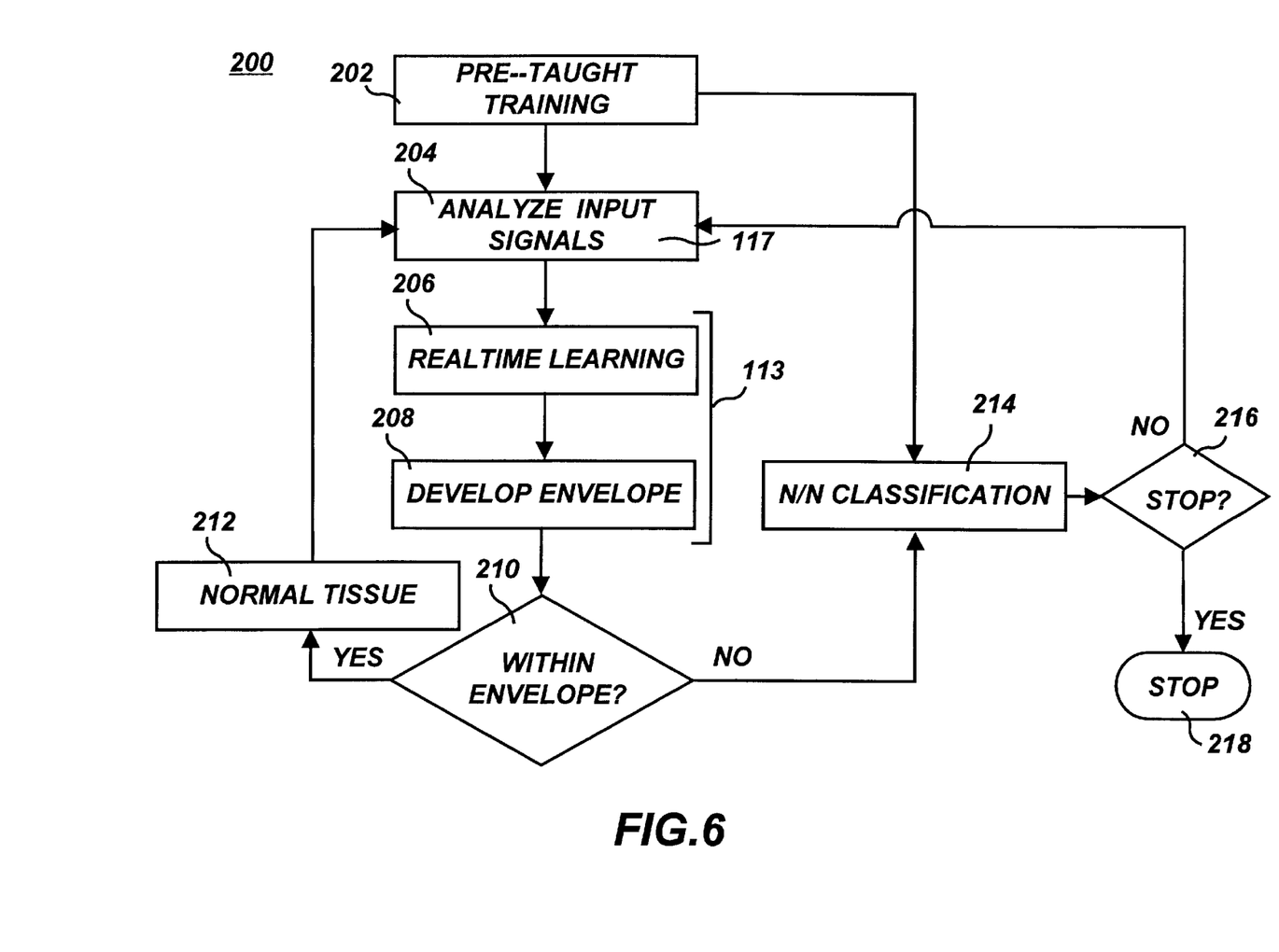
FIG. 6 is a flow chart illustrating the learning process of the heuristic system of FIG. 1.

The neural network module 154 will now be described in greater detail in connection with FIG. 6 which illustrates the learning process 200 of the heuristic system 10. The neural network module 154 is trained (block 202), in combination with the fuzzy logic, to create a model of various types of tissues. The training is carried out using one or a combination of suitable hybrid neural networks, including but not limited to:

Backpropagation.

Radial basis function (RBF).

Infold self organizing feature map.

Cerebellar model articulation computer (CMAC).

For near real-time modeling of brain tissue, radial basis function (RBF), Infold self organizing feature maps and cerebellum model arithmetic computer (CMAC) neural networks are used in various combinations to provide fast learning and enhanced modeling. Data used for learning include (1) instrument sensor data that has been signal processed to provide a set of parameters which captures the main characteristics of the tissue; (2) expert knowledge data that has been processed through fuzzy logic to provide a set of parameters to aid in the modeling of the tissue being penetrated; and (3) tissue identification data provided by pre-trained neural networks to aid in the classification of the tissue being penetrated.

Pre-trained neural networks are neural networks which have been trained using reference tissues and which are continually being updated based on instrument sensor data obtained from surgery and confirmed tissue type from laboratory test results of the biopsied tissue.

As the probe-cannula assembly 27 advances through normal tissue (block 111), the neural network module 154 analyzes the input signals (block 204) from the instrument 16, and learns, on a near real-time basis (block 206), the specific properties of the normal tissue for the particular subject. The neural network module 154 then develops an envelope or model for the specific properties learned (block 208). The neural network module 154 has the ability to develop a separate envelope for each of the parameters or factors being sensed.

The neural network module 154 then places the envelope on top of the learned model to define the normal range of the specific properties of the normal tissue, and to further identify the range of the properties of abnormal tissue. The neural network module 154 then compares the input signals acquired by the instrument 16 to the envelope and determines whether the input signals fall within the envelope (block 210). If the input signals fall within the normal tissue range defined by the envelope, the neural network module identifies the tissue penetrated as normal tissue (block 212), and the computer system 20 instructs the instrument to keep advancing the probe-cannula assembly 27 toward the target site (block 115).

As the probe-cannula assembly 27 advances through the tissue the neural network module 154 continues learning on a near real-time basis and updating the envelope. The foregoing routine (blocks 204, 206, 208, 210) is repeated for each of the envelopes (if more than one envelope have been developed) until the neural network module 154 determines that the input signals fall outside one or a combination of envelopes of normal properties.

Once such determination is made the neural network module 154 compares the input signals to the pre-taught training model and classifies the tissue type (block 214). For example, identification of abnormal brain tissue is determined by detection of change and comparison with previously learned models of abnormal brain tissues. The computer system 20 then inquires whether or not to stop the advancement of the probe-cannula assembly 27 (block 216). If the surgeon determines that further advancement is required then the routine of data collection, analysis and classification (blocks 204, 206, 208, 210, 214) is continued until such time as the surgeon instructs the computer system 20 to stop the advancement of the probe-cannula assembly 27 (block 218). In certain applications it might be desirable to have the probe-cannula assembly 27 penetrate the abnormal tissue (or tumor) completely and extend beyond it.

The operation of the multimodality system 10 is controlled through the user friendly three-dimensional (3D) graphics interface 158. Real-time tissue identification information is also displayed graphically. Patient data is presented in a three dimensional stereographics display 161. Acoustic feedback of selected information is provided as an aid to the surgeon. Upon detection of the close proximity to blood vessels or abnormal brain tissue, the actuator mechanism 26 immediately stops the probe penetration. The 3D stereographics display 161 is comprised of three orthogonal views of the anatomy, with each view presenting the appropriate sequence stack of MRI or CT scans. In each view, a graphical model of the probe is driven in motion in real-time by data incoming from the probe. In addition, the multisensory outputs from the actual probe are displayed graphically in real-time at the probe tip in each view. A closeup of the probe tip is provided to show fine details of the MRI or CT scans as the probe approaches each layer. These views provide a virtual reality environment for visualizing the approach to the target site and the probe proximity to critical arteries.

The 3D graphics interface 158 further includes an indicator 163 for the robotics system that provides an indication as to the status and trend analysis of the system 10. The 3D graphics interface 158 may also provide access to patient records or data, to remote surgery experts and to various databases.

In another embodiment for diagnosis or surgery where robotic insertion is not advantageous, the probe as described above can be a hand-held device inserted by hand into the subject.

While specific embodiments of the present system were illustrated and described in accordance with the present invention, modifications and changes of the system dimensions, use and operation will become apparent to those skilled in the art, without departing from the scope of the invention.

What is claimed is:

1. A system comprising in combination:
   (a) an instrument including:
      (i) a probe-cannula assembly formed of a multimodality probe and a cannula, with said probe being lodged at least in part within said cannula; and
      (ii) one or more sensors and tools housed at least in part within said probe; and
   (b) a computer system including:
      (i) an instrument control unit for generating instructions to said instrument, said instrument control unit being connected to said instrument;
      (ii) a neural network module for adaptively learning information derived by said instrument and for providing at least near real-time modeling;
      (iii) a central processing unit for acquiring data from said instrument and said neural network module, and for processing signals to said instrument, and neural network module.

2. The system according to claim 1 including:
   (c) a retention device,
   (d) an actuator mechanism secured to said retention device, and attached to said probe-cannula so as to make said probe-cannula automatically drivable by said actuator mechanism,
   (e) control circuitry for powering said actuator mechanism, and
   (f) an instrument control unit within said computer system for generating instructions to said control circuitry.

3. The system according to claim 2, wherein said actuator mechanism includes two motors that automatically drive said probe inside said cannula, and that further advance said probe-cannula assembly in a predetermined direction.

4. The system according to claim 3, wherein said retention device is a stereotactic device for mounting on a subject.

5. The system according to claim 4, wherein said instrument further includes a mounting structure; a guide mechanism; a probe mounting plate; and a cannula mounting plate.

6. The system according to claim 5, wherein said mounting structure includes a base that removably and adjustably mates with said retention device.

7. The system according to claim 6, wherein said guide mechanism includes at least one guide rail for allowing said probe mounting plate to journey slidably in a predetermined direction.

8. The system according to claim 1, wherein said computer system further includes a fuzzy logic interface to said neural network module, said fuzzy logic interface providing means for incorporating expert medical knowledge.

9. The system according to claim 4, wherein said neural net provides means for processing information derived by said instrument including any of: tissue resistance, color, pressure, tissue reflectance.

10. The system according to claim 9, wherein said computer system further includes a three-dimensional graphics interface.

11. The system according to claim 8, wherein said neural network module provides means for identifying abnormal tissue by detecting a change of one or more factors relative to previously learned models of abnormal tissue.

12. The system according to claim 11, wherein said one or more sensors and tools are selected from a group comprising:
- a strain gauge;
- a wick in needle pressure sensor;
- a laser Doppler blood flow sensor;
- an ultrasound probe;
- an endoscope;
- a partial pressure of oxygen sensor;
- an optical sensor;
- a temperature sensor;
- an ion specific sensor;
- a microelectrode;
- a tissue ablation laser;
- an effector.

13. The system according to claim 12, wherein from said one or more sensors and tools an effector is selected and wherein said effector includes any one of: biopsy forceps; malleable biopsy forceps: grasping forceps; micro-scissors; a coagulator; an irrigator.

14. The system according to claim 13, wherein based on said derived information, said computer system provides means for determining whether it has detected tissue property changes or blood vessels.

15. The system according to claim 14, wherein if said computer system has detected tissue property changes said neural network module provides means for comparing said information to previously learned information and properties.

16. The system according to claim 15, wherein said neural network module is provided with means for being trained by any one or a combination of neural networks, and a fuzzy logic interface to said neural network module is used to incorporate expert medical knowledge in the learning process.

17. The system according to claim 16, wherein said neural networks are selected from the group comprising: back propagation; self organizing maps; cerebellum model arithmetic computer; radial basis function.

18. The system according to claim 17, wherein said neural network module provides means for adaptively learning information derived by said instrument by further:
- developing one or more envelopes corresponding to one or more specific properties learned; and
- identifying properties of abnormal tissue.

19. The system according to claim 18, wherein when said computer system provides means for identifying abnormal tissue by comparison with previously learned models of abnormal tissues.

20. The system according to claim 11, wherein said neural network module provides means for adaptively learning information derived by said instrument by:
- advancing said probe-cannula assembly into normal tissue;
- advancing said probe-cannula assembly toward a predetermined target site;
- said computer system continually checking to determine whether changes in tissue properties or blood vessels have been detected;
- if said computer system does not detect property changes or blood vessels, it instructs said probe-cannula assembly to continue its travel toward said target site; and
- if said computer system detects property changes or blood vessels, it instructs said probe-cannula assembly to stop advancing.

21. The system of claim 1, said probe-cannula assembly configured such that said probe is removable from the cannula assembly during an application and replaceable by a second probe having replacement one or more sensors and tools.

* * * * *